United States Patent [19]

Nordlund et al.

[11] Patent Number: 4,874,744

[45] Date of Patent: Oct. 17, 1989

[54] METHOD OF USING MELANOCYTE STIMULATING HORMONE AS DERMATIS TREATMENT

[75] Inventors: James J. Nordlund; Lawrence A. Rheins, both of Cincinnati, Ohio

[73] Assignee: University of Cincinnati, Cincinnati, Ohio

[21] Appl. No.: 323,606

[22] Filed: Mar. 13, 1989

[51] Int. Cl.$^4$ .................. A61K 37/02; C07K 7/08
[52] U.S. Cl. .................................. 514/13; 514/14
[58] Field of Search ........................... 514/13, 14

[56] References Cited

U.S. PATENT DOCUMENTS

| | | | |
|---|---|---|---|
| 4,444,762 | 4/1984 | Rajadhyasksha | 514/274 |
| 4,593,038 | 6/1986 | Burzynski | 514/328 |
| 4,755,535 | 7/1988 | Minaskanian et al. | 514/270 |

FOREIGN PATENT DOCUMENTS

| | | | |
|---|---|---|---|
| WO87/04623 | 8/1987 | PCT Int'l Appl. | 514/14 |
| WO88/0498-68 | 3/1988 | PCT Int'l Appl. | 514/14 |

OTHER PUBLICATIONS

Rheins et al: The Journal of Immunology, vol. 136, No. 3, Feb. 1, 1986.
Rheins et al: Cellular Immunology 106, 33–42 (1987).
Robertson et al: Inflammation, vol. 10, No. 4, 1986.
Ali et al: Abstracts, vol. 87, No. 3, 9/86, p. 413.
Cannon et al: Journal of Immunology, vol. 137, 2232–2236, No. 7, Oct. 1, 1986.

*Primary Examiner*—Lester L. Lee
*Attorney, Agent, or Firm*—Wood, Herron & Evans

[57] ABSTRACT

Dermatitis is treated by topically applying a composition including melanocyte stimulating hormone to the epidermal portion of the infected skin. Preferably, alpha-melanocyte stimulating hormone is applied in a concentration in the range of about $5 \times 10^{-5} M/cm^2$. This is an effective treatment against a broad range of dermatitis. Occlusion of the affected site enhances response.

9 Claims, No Drawings

METHOD OF USING MELANOCYTE STIMULATING HORMONE AS DERMATIS TREATMENT

Dermatitis refers to a large number of inflammatory conditions of the skin which have a variety of different causes. There is for example atopic dermatitis which is genetic in origin. Contact dermatitis is caused by common agents such as nickel, poison ivy, poison oak, turpentine. Industrial contact dermatitis refers to dermatitis caused by contacting irritating or allergic substances during ones occupation. Berlock dermatitis is an inflammation caused by an allergic reaction to a perfume or other toiletry. There are also other types of dermatitis such as infectious eczematoid dermatitis, medicamenta dermatitis caused by allergic reaction to a medicine, schistozomal dermatitis caused by penetration to the skin of larval form of schistozomes, seborrheic dermatitis which is an inflammatory skin disease with scaling and itching.

There are various treatments for each of these types of dermatitis. However, to date melanocyte stimulating hormone (MSH) has never been used to treat dermatitis. Alpha-MSH neuropeptide of approximately 13 amino acids has been suggested as a tanning agent since it encourages the production of pigment containing cells. More recently alpha-MSH has been shown to have other functions for example the modulation of immune inflammatory processes. Further it has an antipyrogenic effect and also blocks hepatic induction of acute phase reactants including C reactive protein and serum amyloid. However, no MSH and in particular alpha-MSH has never been applied to the epidermal layer of the skin to treat dermatitis.

SUMMARY OF THE INVENTION

The present invention is premised on the realization that dermatitis can be treated by topically applying melanocyte stimulating hormone (MSH) to the epidermal layer of dermatitis affected skin. More particularly, the present invention is premised on the realization that by applying approximately $1 \times 10^{-2}$M/cm$^2$ to $1 \times 10^{-10}$M/cm$^2$ of melanocyte stimulating hormone one can effectively treat dermatitis including atopic dermatitis, nummular dermatitis, dermatitis medicamentosa, seborrheic dermatitis, contact dermatitis and so on. This agent provides a treatment for all forms of dermatitis in general.

DETAILED DESCRIPTION OF THE INVENTION

Melanocyte stimulating hormone refers to a polypeptide having the following seven peptide sequence: HIS-PHE-ARG-TRP-GLY-LYS-PRO.

Serine may be substituted for Glycine and Valine alanine or serine may be substituted for the Lysine. Specific example of alpha and beta MSH and their sources are listed below:

| Species | Structure |
| --- | --- |
| a-MSH | |
| Mammals | Ac$_2$—Ser-Tys-Ser-Met-Glu-His-Phe-Arg-Trp-Gly-Lys-Pro-Val-NH$_2$ |
| Mammals | Ac—Ser-Tyr-Ser-Met-Glu-His-Phe-Arg-Trp-Gly-Lys-Pro-Val-NH$_2$ |
| Mammals | H—Ser-Tyr-Ser-Met-Glu-His-Phe-Arg-Trp-Gly-Lys-Pro-Val-NH$_2$ |
| Salmon 1 | H—Ser-Tyr-Ser-Met-Glu-His-Phe-Arg-Trp-Gly-Lys-Pro-Val-NH$_2$ |
| Salmon 2 | Ac—Ser-Tyr-Ser-Met-Glu-His-Phe-Arg-Trp-Gly-Lys-Pro-Ile-Gly-His-OH |
| Dogfish | H—Ser-Tyr-Ser-Met-Glu-His-Phe-Arg-Trp-Gly-Lys-Pro-Met-NH$_2$/OH |
| B-MSH | |
| Macacus | H—Asp-Glu-Gly-Pro-Tyr-Arg-Met-GLu-His-Phe-Arg-Trp-Gly-Ser-Pro-Pro-Lys-Asp-OH |
| Porcine | H—Asp-Glu-Gly-Pro-Tyr-Lys-Met-Glu-His-Phe-Arg-Trp-GLy-Ser-Pro-Pro-Lys-Asp-OH |
| Equine | H—Asp-Glu-Gly-Pro-Tyr-Lys-Met-Glu-His-Phe-Arg-Trp-Gly-Ser-Pro-Arg-Lys-Asp-OH |
| Bovine | H—Asp-Ser-Gly-Pro-Tyr-Lys-Met-Glu-His-Phe-Arg-Trp-Gly-Ser-Pro-Pro-Lys-Asp-OH |
| Sheep | H—Asp-Ser-Gly-Pro-Tyr-Lys-Met-Glu-His-Phe-Arg-Trp-Gly-Ser-Pro-Pro-Lys-Asp-OH |
| Camel 1 | H—Asp-Gly-Gly-Pro-Tyr-Lys-Met-Glu-His-Phe-Arg-Trp-Gly-Ser-Pro-Pro-Lys-Asp-OH |
| Camel 2 | H—Asp-Gly-Gly-Pro-Tyr-Lys-Met-Gln-His-Phe-Arg-Trp-Gly-Ser-Pro-Pro-Lys-Asp-OH |
| Salmon 1 | H—Asp-Gly-Ser-Tyr-Lys-Met-Asn-His-Phe-Arg-Trp-Ser-Gly-Pro-Pro-Ala-Ser-OH |
| Salmon 2 | H—Asp-Gly-Ser-Tyr-Arg-Met-Gly-His-Phe-Arg-Trp-Gly-Ser-Pro-Thr-Ala-Ile-OH |
| Dogfish 1 | H—Asp-Gly-Asp-Asp-Tyr-Lys-Phe-Gly-His-Phe-Arg-Trp-Ser-Val-Pro-Leu-OH |
| Dogfish 2 | H—Asp-Gly-Ile-Asp-Tyr-Lys-Met-Gly-His-Phe-Arg-Trp-Gly-Ala-Pro-Met-Asp-Lys-OH |

Preferably, the MSH in alpha-MSH which has the following peptide sequence:
AC-SER-TYR-SER-MET-GLU-HIS-PHE-AGR-TRP-GLY-LYS-PRO-VAL-NH$_2$.

The initial serine may be biacetylated or non-acetylated. This hormone is secreted by pars intermedia of the pituitary gland. Alpha-MSH can be either synthesized or extracted from animal tissue where it is derived from a larger peptide known as adrenocorticotrophin hormone (ACTH). ACTH itself is derived from a larger molecule called proipromelanocorten. Alpha MSH can also be purchased from the following companies as 100% pure. Sigma Chemical, St. Louis, Mo.

The MSH for use is combined with a carrier. The preferred concentration of the MSH in the carrier is from $1 \times 10^{-2}$M to $1 \times 10^{-10}$M.

There is a large list of acceptable carriers. Any pharmacologically acceptable carrier in which the MSH can be dispersed can be used such as propylene glycol, lanolin, fatty acids, emulsified fatty acids, polyethylene glycol, water, petrolatum, aquaphilic ointment and cream, acid mantle cream. Its efficacy will be enhanced by occlusion with standard Telfa dressings; or special occlusion dressings such as Saran wrap or artificial biological membranes like Actiderm.

In addition to the above, the medicament of the present invention can include antioxidants, antibacterials, stabilizers and the like such as butylated hydroxy toluene, butylated hydroxy anisole, sorbic acid and others. Penetration enhancing agents such as retenoic acid, salicylic acid and alpha hydroxy acids can be added.

The present medicament is suitable for treatment of all forms of dermatitis including atopic dermatitis, contact allergies which may be caused by a variety of different allergens including dinitrofluorobenzene, oxazalone, nickel, poison ivy, poison oak, dies, perfumes and scents, petroleum extracts and products such as turpentine.

The medicament can be applied directly to the epidermal layer of the skin by rubbing it into the skin either prior to inflammation to prevent a dermatalogical reaction with a contact allergen or to reduce inflammation from any cause. It can also be applied after inflammation has been initiated for example by exposure to agent such as an allergen causing dermatitis or from atopic dermatitis. The application should be repeated two to three times a day until the dermatitis is relieved or the contact with the allergen is discontinued. Occlusive dressings may be helpful.

To test the present invention mammals, specifically mice, were tested. Five to seven week old male C57BL/6(H-2$^B$) mice were purchased from the Charles River Laboratory, Wilmington, MA and were housed in AAALAC approved animal facilities, four per cage with free access to water and Purina mouse chow. The animals were maintained on a 12 hour light/dark photo period. All experiments were performed at least twice with similar results.

Groups of mice, four per group, were treated on shaved back with 50 ml of $10^{-5}$M alpha-MSH or diluent (propylene glycol) on days 1-5. One half hour following the last treatment, treated and diluent control mice were sensitized with either 20 ml of 0.5% (0.5 gm/dl) 2,4-dinitro-1-fluorobenzene (DNFB) (Sigma Chemical Co., St. Louis, MO) in a 4:1 acetone-olive oil mixture or with 25 ml of 10% 4 ethoxymethyl 2-phenyloxazol-5-1 (oxazalone hereinafter ox) applied to the shaved back epideral site. On day 6, mice were sensitized again with the respective haptens, DNFB or OX and rested for five days. On day 11, ears of treated and control mice were measured as baseline. The ears were challenged with 20 ml of 0.2% (0.2 g/dl) DNFB or 20 ml of 1% (1 g/dl) OX. On day 12, the ear thickness was measured a second time. Percent suppression was calculated by the formula:

percent suppression=[1-(experimental-negative control) over positive control (diluent)-negative controls)]×100%. Elicitation of the CHS response was carried out similarly except the animals were treated on days 1-5 with 50 ml of $10^{-5}$M alpha-MSH or propylene glycol and then sensitized on the untreated shaved backs with either DNFB or OX.

The groups of mice that were treated with alpha-MSH on dorsal skin demonstrated 64% suppression in ear thickness in animals treated with DNFB and 99% suppression in ear swelling following OX treatment versus control mice. Negative control animals did not show any significant difference in the ear swelling and serve as an indicator for the irritant effects of the DNFB allergen. Other negative control mice challenged only with OX demonstrated similar CHS responsiveness as the DNFB negative control mice. Further, experiments demonstrated that the diluent propylene glycol when applied alone without MSH produced no effects on either the sensitization or elicitation limbs of the CHS response or on the number of Ia+Thy1.2+dendritic cells. The results confirm that the epicutaneous application of alpha-MSH can abrogate sensitization to two different highly potent antigens resulting in an absence of an elicitation response at a distal challenge site.

Elicitation of inflammatory components of contact hypersensitivity responsiveness were assessed in previously sensitized animals whose ears were treated on days 1-5 with 50 ml of $10^{-5}$M alpha-MSH or propylene glycol. Animals were previously sensitized with DNFB on the untreated shaved back and challenged on day 11 as described above. Twenty-four hours post-DNFB challenge the alpha-MSH treated ears demonstrated 61% suppression in ear swelling over control mice. This demonstrates alpha-MSH can suppress pre-existing allergies or inflammation.

To determine if the alpha-MSH treatment was a local effect or in contrast a systemic reactivity, C57BL/6 mice were treated with alpha-MSH on the shaved dorsal surface for five days followed by sensitization with DNFB on the untreated shaved abdomen and challenged on day 11 on the ears as was performed in the earlier experiments. There were no significant changes in ear thickness in treatment versus diluent control mice. It would appear from these data that topically applied alpha-MSH at the dose applied under those specific experimental conditions in vivo seems to act locally and does not produce systemic immune suppression.

These experiments demonstrate the effectiveness of topical application in suppressing allergen caused inflammation, both prior to and subsequent to contact. This provides an extremely useful medicament for treatment of dermatitis. The preceding has been a description of the present invention as well as the preferred method currently known of practicing this invention. However, the invention shall be defined only by the appended claims wherein

We claim:

1. A method of treating dermatitis of a mammal comprising applying an effective amount of melanocyte stimulating hormone to a dermatitis affected portion of said mammal's epideral layer.

2. The method claimed in claim 1 wherein said melanocyte stimulating hormone is alpha-MSH.

3. The method claimed in claim 2 wherein the dermatitis affected portion is inflamed.

4. The method claimed in claim 2 wherein said effective amount of alpha-melanocyte stimulating hormone is from about $1\times10^{-2}$M/cm$^2$ $-1\times10^{-10}$M/cm$^2$ per three hour period of time.

5. A method of treating an inflamed epidermis caused by a contact allergen comprising applying an effective amount of an alpha-melanocyte stimulating hormone to said inflamed epidermis.

6. The method claimed in claim 5 wherein said effective amount is from about $1\times10^{-2}$M/cm$^2$ to about $1\times10^{-10}$M/cm$^2$ per three hour period.

7. A method of preventing inflammation of mammalian epidermis caused by contact with an allergen comprising maintaining an effective amount of melanocyte stimulating hormone on said epidermis during contact by said epidermis with said allergen.

8. The method claimed in claim 7 wherein said melanocyte stimulating hormone is alpha-MSH.

9. The method claimed in claim 2 wherein said alpha-MSH is applied by occlusion.

* * * * *

UNITED STATES PATENT AND TRADEMARK OFFICE
CERTIFICATE OF CORRECTION

PATENT NO. : 4,874,744
DATED : October 17, 1989
INVENTOR(S) : James J. Nordlund et al.

It is certified that error appears in the above-identified patent and that said Letters Patent is hereby corrected as shown below:

Please insert on the Title page, column 1, immediately after the title, --Research leading to the present invention was funded in part by the National Institute of Health Grant No. AM-25252. Accordingly, the United States Government has certain rights in the invention.--

Signed and Sealed this

Thirteenth Day of December, 1994

Attest:

BRUCE LEHMAN

Attesting Officer

Commissioner of Patents and Trademarks